US005624659A

United States Patent [19]

Bigner et al.

[11] Patent Number: 5,624,659
[45] Date of Patent: Apr. 29, 1997

[54] METHOD OF TREATING BRAIN TUMORS EXPRESSING TENASCIN

[75] Inventors: Darell D. Bigner; Michael R. Zalutsky, both of Chapel Hill, N.C.

[73] Assignee: Duke University, Durham, N.C.

[21] Appl. No.: 392,419

[22] Filed: Feb. 22, 1995

Related U.S. Application Data

[63] Continuation of Ser. No. 33,827, Mar. 19, 1993, abandoned.

[51] Int. Cl.$^6$ .................. A61K 51/10; A61K 39/395; C07K 16/28; C07K 16/30
[52] U.S. Cl. ............. 424/1.49; 530/391.3; 530/391.1; 530/388.8; 530/389.7; 530/388.85; 530/389.1; 424/178.1; 424/181.1
[58] Field of Search ................. 530/391.3, 388.8, 530/389.1, 389.7, 388.85, 391.7, 391.1; 424/155.1, 178.1, 179.1, 183.1, 1.49

[56] References Cited

PUBLICATIONS

Halperin, Int. J. Radia. Oncol. Biol. Phys., 1988, 15:505.
Goldenberg, CA Cancer J Clin., 1994, 44:43.
Papanastassiou et al., Medlars Database, Mar. 1992.
Riva et al., Int. J. Cancer, 51:7, Apr. 1992.
M. Bourdon et al., Cancer Research 43, 2796–2805 (1983).
L. S. Lashford et al., Cancer 61, 857–868 (1988).
R.P. Moseley et al., Br. J. Cancer 62, 637–642 (1990).
R.P. Moseley et al., Int. J. Cancer 52, 38–43 (1992).
V. Papanastassiou et al., J. Neurooncology 12, 268 (1992).
P. Riva et al., Nuclear Medicine Communications 13, 635 (1992).
J. M. Schuster et al., Cancer Research 57, 4164–4169 (1991).
M.R. Zalutsky et al., Cancer Research 49, 5543–5549 (1989).
E.V. Colapinto et al., Cancer Research 50, 1822–1827 (1990).
Riva et al., Int. J. Cancer, 51:7, 1992.
Zalutsky et al., Cancer Res., 50:4105, 1990, Monoclonal . . . Administration .
Zalutsky et al., Cancer Res., 49:2807, 1989, Pharmacokinetics . . . Malignancies.
Harris et al., Tibtech, 11:42, 1993, Therapeutic . . . Age.
Osband et al., Immunol. Today, 11:193, 1990, Problems . . . immunotherapy.
Hird et al., In Genes & Cancer, 1990 pp. 183–189.
Neuwelt et al., Cancer Res., 48:4725, 1988, Delivery . . . Disruption.

Y.S. Lee et al; Therapeutic Efficacy of Antiglioma Mesenchymal Extracellular Matrix $^{131}$I–Radiolabeled Murine Monoclonal Antibody in a Human Glioma Xenograft Model, Cancer Research 48, pp. 559–566 (1988).
Y. Lee et al; Treatment of Intracranial Human Glioma Xenografts with $^{131}$I–labeled Anti–Tenascin Monoclonal Antibody 81C6$^1$, Cancer Research 48, pp. 2904–2910, May 15, 1988.
S. Clifford Shold, et al; Distribution and Dosimetry of I–123–Labeled Monoclonal Antibody 81C6 in Patients with Anaplastic Glioma, Investigative Radiology 28, pp. 488–496 (1993).
R. D. McComb, et al; Distribution of Type VI Collagen in Human Gilomas: Comparison with Fibronectin and Giloma–Mesenchymal Matrix Glycoprotein, Journal of Neuropathology and Experimental Neurology 46 pp. 623–633 (1987).
R.G. Blasberg, et al; Regional Localization of a Glioma–associated Antigen Defined by Monoclonal Antibody 81C6 in Vivo: Kinetics and Implications for Diagnosis and Therapy, Cancer Research 47, pp. 4432–4443 (Aug. 15, 1987).
M. A. Bourbon et al; Monoclonal Antibody Localization in Subcutaneous and Intracranial Human Glioma Xenografts: Paired–Label and Imaging Analysis, Anticancer Research 4, pp. 133–140 (1984).
D.E. Bullard, et al; Specific Imaging of Human Brain Tumor Xenografts Utilizing Radiolabelled Monoclonal Antibodies (MAbs), Nuklearmedizin 25, pp. 210–215 (1986).
C.J. Wikstrand, et al; Comparative localization of glioma–reactive monoclonal antibodies in vivo in an athymic mouse human glioma xenograft model, Journal of Neuroimmunology 15, pp. 37–56 (1987).

Primary Examiner—Frank C. Eisenschenk
Attorney, Agent, or Firm—Bell, Seltzer, Park & Gibson

[57] ABSTRACT

Methods of treating solid and cystic tumors are disclosed. The method comprises administering to a subject afflicted with a cystic tumor an antibody which binds to tenascin in a therapeutically effective amount. The administering step is carried out by depositing the antibody in the cyst cavity of the cystic tumor. For solid tumors, disclosed is a method involving first, removing a solid tumor from a solid tissue organ of an afflicted subject; then forming an enclosed resection cavity in the organ of the subject at the location from which the solid tumor was removed; and then administering to the subject an antineoplastic agent by depositing the antineoplastic agent in the resection cavity. Particularly preferred for carrying out the foregoing is the monoclonal antibody 81C6 and antibodies which bind to the epitope bound by monoclonal antibody 81C6.

21 Claims, 3 Drawing Sheets

81C6 HEAVY CHAIN VARIABLE REGION SEQUENCE

```
                                                              *********
CTGGACTAGGTTCTTATGTAAGAAGTCCCCTGCTCATCATTATGCAAATTACCTGAGTCT      60

ATGGTGATTAAAACAGGGATGTCCACACCCTTAAATCAACGACGATCAGTGTCCTCTCC     120
 M-20 E  V  S  W  I  F  L  F  L  L
AAAGTCCCTGAACACACTGACTCTAACCATGGAGTTGGATATTCTTTCTCCT            180
   S   G   T   A     M-20 E  V  S  W  I  F  L  F  L  L
GTCAGGAACTGCAGGTAAGGGCTCACCAGTTCAAATCTGAAGTGGAGACAGGACCTGA     240
                                            G-4 V  H  S  E+1 V  Q  L
GGTGACAATGACATCTACTCTGACATTCTCTCCTCAGGTGTCCACTCTGAGGTCCAGCTG   300
                                         Q  Q  C
CAGCAGTCTGGACCTGAGCTGGTAAAGCCTGGGGCTTCAGTGAAGATGTCCTGCAAGGCT   360
 Q  Q  S  G  P  E  L  V  K  P  G  A  S  V  K  M  S  C  K  A
TCTGGATACACATTCACTAGCTATGTTGTGCACTGGGTGAAGCAGAAGCCTGGGCAGGGC   420
 S  G  Y  T  F  T  S  Y  V  V  H  W  V  K  Q  N  P  G  Q  G
CTTGAGTGGATTGGATATATTAATCCTTTCAATGATGGTACTAAGTACAATGAGAACTTC   480
 L  E  W  I  G  Y  I  N  P  F  N  D  G  T  K  Y  N  E  N  F
AAAGGCAAGGCCACACTGACTTCAGACAGATCCTCCAGCACAGCCTACATGGAGCTCAGC   540
 K  G  K  A  T  L  T  S  D  R  S  S  S  T  A  Y  M  E  L  S
AGCCTGACCTCTGAGGACTCTGCGGTCTATTTCTGTGCAAGAGACATGGGTCGGGAAGGC   600
 S  L  T  S  E  D  S  A  V  Y  F  C  A  R  D  M  G  R  E  G
TTTGCTTACTGGGGCCAAGGGACTCTGGTCACTGTCTCTGCAGGTGAGTCCTAACTTCTC   660
 F  A  Y  W  G  Q  G  T  L  V  T  V  S  A
```

FIG. 2A.

81C6 LIGHT CHAIN VARIABLE REGION SEQUENCE
**********

```
TATCAACCAGGAGATTTGCATATTGCTCCCTAGGAGGACCTCTTCTTGCAGGTGCAGGG                                    60

TAAAAGCTCACTCTCCTCTTTCTGTCTTGATTACTTTGACTCACCATATCAAGTTCGCAGA                                 120
M-20R F  S  A  Q  L  L  G  L  L  L  V  L  I  P
     ATGAGGTTCTCTGCTCAGTTGCTTGGGGCTGCTTGTGCTCTGGATCCCTGGTAAGGAGACA                             180

AAGATGAAGAAGGAGAATTTGAGGGAGGGGATTTCTGAGACATGATGATAAATATGTA                                    240

TGTTCTGTACATGTCTGAGATATACAGTTCTGTTCTCCAGTAAAGGACTTGTGAGGTTCA                                  300

AAGTGTGAAGAGATTAAGGTCTGTTTTTCTGTGACAACTCTGACAGTTCCAAAGCCAAAA                                  360

GTCAAATGAAGAGACTCTCTGCTTCCTCTACATGCATATTTTATGTGGAGCACTTCT                                     420

AGAGTATGAGTGAAAGACATGAACAAAATAAGTAGAACAAAATAAGGAAAGAAATTCAC                                   480
                                                            G-4 S  T  A  D+1
TTCATCGTATCATTTTTACATAACCAATTAATTCTCTTATTGCAGGATCCACTGCAGA                                    540
I  V  M  T  Q  A  A  F  S  N  P  V  T  L  G  T  S  A  S  I
      TATTGTGATGACGCAGGCTGCATTCTCCAATCCAGTCACTCTTGGAACATCAGCTTCCAT                             600
                                                        Y  L  Y  W  Y
S  C  R  S  S  K  S  L  L  H  S  N  G  I  T  Y  L  Y  W  Y
CTCCTGCAGGTCTAGTAAGAGTCTACTACATAGTAATGGCATCACTTATTTGTATTGGTA                                  660
                                                L  A  S
L  Q  K  P  G  Q  S  P  Q  L  L  I  Y  Q  M  S  N  L  A  S
TCTGCAGAAGCCAGGCCAGTCCTCAGCTCCTGATTTATCAGATGTCCAACTTGCCTC                                     720
                                                            R  I  S
G  V  P  D  R  F  S  S  S  G  S  G  T  D  F  T  L  R  I  S
AGGAGTCCCAGACAGGTTCAGTAGCAGTGGGTCAGGAACTGATTTCACACTGAGAATCAG                                  780
R  V  E  A  E  D  V  G  V  Y  Y  C  A  Q  N  L  E  L  P  R
CAGAGTGGAGGCTGAGGATGTGGGTGTTATTACTGTGCTCAAATCTAGAACTTCCTCG                                    840
T  F  G  G  T  K  L  E  I  K
GACGTTCGGTGGAGGCACCAAGCTGGAAATCAAACGTAAGTA                                                    882
```

METHOD OF TREATING BRAIN TUMORS EXPRESSING TENASCIN

This invention was made with government support under grant numbers R37-CA11898 from the National Institutes of Health, NS20023 from the National Institutes of Health, CA56115 from the National Institutes of Health, and CA42324 from the National Institutes of Health. The government has certain rights to this invention.

This is a continuation of application Ser. No. 08/033,827 filed on Mar. 19, 1993, now abandoned.

FIELD OF THE INVENTION

The present invention relates to the treatment of cancer, and particularly relates to the treatment of cystic brain tumors and cystic brain tumor resection cavities with anti-tenascin antibodies such as 81C6.

BACKGROUND OF THE INVENTION

Despite years of intensive investigation, the prognosis for most patients with primary anaplastic central nervous system (CNS) tumors remains poor. Median survival for adults with the most common form of CNS tumor, the glioblastoma multiforme, is 8–12 months. The outlook is somewhat better for less common tumors such as anaplastic astrocytoma and medulloblastoma, but most primary anaplastic CNS tumors are highly resistant to currently available therapy.

Only radiotherapy has been shown to prolong survival in patients with anaplastic gliomas. Following conventional therapy with surgery and external beam radiotherapy, malignant gliomas tend to recur at or near the original tumor site. Temporarily implanted radioactive iodine sources (interstitial brachytherapy) have recently been used to deliver high dose focal radiotherapy to locally recurrent malignant gliomas.

The possibility of utilizing therapeutic antibodies in the treatment of cancer is beginning to be investigated. R. Moseley et al., *Br. J. Cancer* 62, 637 (1990) describe the intrathecal administration of $^{131}$I radiolabelled monoclonal antibody for the treatment of neoplastic meningitis. The treatment of a patient afflicted with melanoma with Mel-14 is described (see also L. Lashford, *Cancer* 61, 857 (1988)). Nevertheless, satisfactory treatments are not yet available, and there is a continued need for new treatments for these diseases.

SUMMARY OF THE INVENTION

In accordance with the foregoing, a first aspect of the present invention is a method of treating a cystic brain tumor. The method comprises administering to a human subject afflicted with a cystic brain tumor (e.g., one which expresses tenascin) an antibody that binds to tenascin in a therapeutically effective amount. The administering step is carried out by depositing the antibody in the cyst cavity of the cystic brain tumor.

Also disclosed herein is a method of treating a solid tumor which comprises, first, removing a solid tumor (e.g., one which expresses tenascin) from a solid tissue organ (e.g., the brain) of an afflicted human subject; then forming an enclosed resection cavity in the organ of the subject at the location from which the solid tumor was removed; and then administering to the subject an antineoplastic agent such as an antibody (e.g., an antibody that binds to tenascin) which is selectively toxic to the cells of the solid tumor in a therapeutically effective amount. The administering step is carried out by depositing the antineoplastic agent in the resection cavity.

Particularly preferred for carrying out the foregoing is the monoclonal antibody 81C6 and antibodies which bind to the epitope bound by monoclonal antibody 81C6.

A further aspect of the present invention is the use of an antibody that binds to tenascin as described herein for the preparation of a medicament for carrying out the treatments described herein.

The foregoing and other objects and aspects of the present invention are explained in detail in the drawings herein and the specification set forth below.

BRIEF DESCRIPTION OF THE DRAWINGS

FIG. 2 shows the nucleotide sequence of 81C6 heavy (FIG. 2A) (SEQ ID NO: 1) and light (FIG. 2B) (SEQ ID NO: 3) chain variable region genes. The nucleotide sequence is numbered in the righthand margin. Nucleotides with asterisks indicate the conserved octanucleotides. The deduced amino acid sequence is above the nucleotide sequence (SEQ ID NO: 3 and SEQ ID NO: 4). Superscript numbers above the amino acid sequence delineate the leader sequence (−20, −4) and the beginning of the actual immunoglobulin sequence (+1). Underlined amino acids indicate where sequence data were obtained by N-terminal amino acid sequencing.

DETAILED DESCRIPTION OF THE INVENTION

Figure 1:
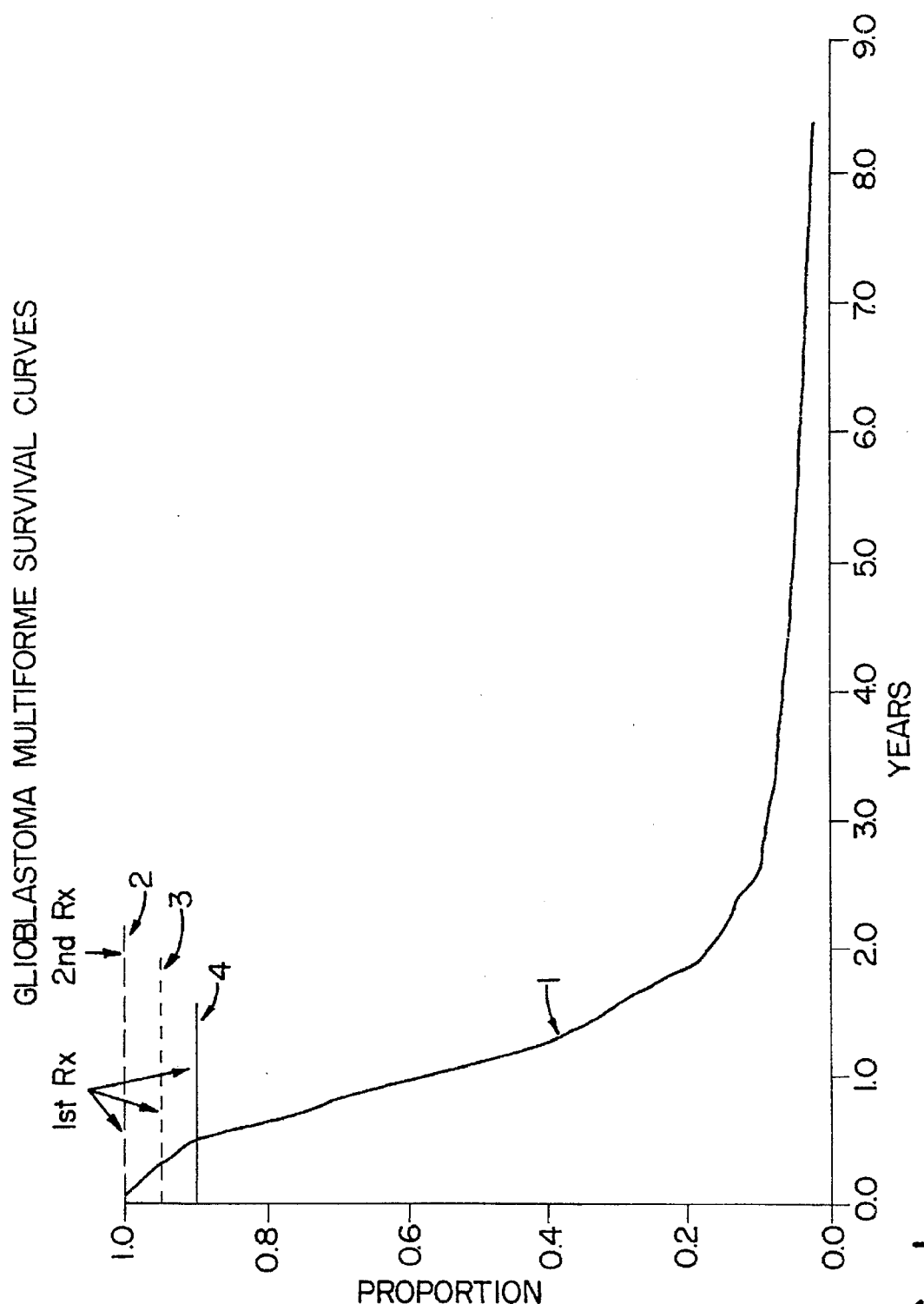
FIG. 1 shows the survival of three human patients treated by the method of the present invention, as compared to the survival curve of a pooled sample of 383 patients treated by previous methods.

Amino acid sequences disclosed herein are presented in the amino to carboxy direction, from left to right. The amino and carboxy groups are not presented in the sequence.

Nucleotide sequences are presented herein by single strand only, in the 5' to 3' direction, from left to right.

A. Antibodies

The term "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be chimeric antibodies. See, e.g., M. Walker et al., *Molec. Immunol.* 26, 403–11 (1989). Such monoclonal antibodies are produced in accordance with known techniques. The term "antibody" as used herein includes antibody fragments which retain the capability of binding to a target antigen, for example, Fab, F(ab')$_2$, and Fv fragments, and the corresponding fragments obtained from antibodies other than IgG. Such fragments are also produced by known techniques.

The monoclonal antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980 (Applicants specifically intend that the disclosure of all U.S. patent references cited herein be incorporated herein by reference).

Monoclonal antibodies may be chimeric antibodies produced in accordance with known techniques. For example, chimeric monoclonal antibodies may be complementarity determining region-grafted antibodies (or "CDR-grafted antibodies") produced in accordance with known techniques.

Monoclonal Fab fragments may be produced in *Escherichia coli* by recombinant techniques known to those skilled in the art. See, e.g., W. Huse, *Science* 246, 1275–81 (1989).

As noted above, antibodies employed in carrying out the present invention are those which bind to tenascin. Particularly preferred are monoclonal antibody 81C6 and antibodies that bind to the epitope bound by monoclonal antibody 81C6 (i.e., antibodies that cross-react with, or block the binding of, monoclonal antibody 81C6). The monoclonal antibody 81C6 is a murine IgG2b monoclonal antibody raised from a hybridoma fusion following immunization of BALB/c mice with the glial fibrillary acidic protein (GFAP) -expressing permanent humanglioma line U-251 MG, as known and described in M. Bourdon et al., *Cancer Res.* 43, 2796 (1983).

B. Therapeutic Antibodies

Monoclonal antibodies used for therapy (i.e., in a method of combatting cancer) may be monoclonal antibodies per se or monoclonal antibodies coupled to a therapeutic agent. Such antibodies are sometimes referred to herein as therapeutic monoclonal antibodies. Any therapeutic agent conventionally coupled to a monoclonal antibody may be employed, including (but not limited to) radioisotopes, cytotoxic agents, and chemotherapeutic agents. See generally *Monoclonal Antibodies and Cancer Therapy* (R. Reisfeld and S. Sell Eds. 1985)(Alan R. Liss Inc. N.Y.). Therapeutic agents may be coupled to the antibody by direct means or indirect means (e.g., via a chelator) by any suitable technique, such as the Iodogen method or with N-succinimidyl-3-(tri-n-butylstanyl)benzoate (the "ATE method"), as will be apparent to those skilled in the art. See, e.g., M. Zalutsky and A. Narula, *Appl. Radiat. Isot.* 38, 1051 (1987).

Examples of radioisotopes which may be coupled to a therapeutic monoclonal antibody include, but are not limited to, $^{131}I$, $^{90}Y$, $^{211}At$, $^{212}Bi$, $^{67}Cu$, $^{186}Re$, $^{188}Re$, and $^{212}Pb$. Examples of chemotherapeutic agents which may be coupled to a therapeutic monoclonal antibody include, but are not limited to, methotrexate. Examples of cytotoxic agents which may be coupled to a therapeutic monoclonal antibody include, but are not limited to, ricin (or more particularly the ricin A chain).

It will be appreciated that monoclonal antibodies per se which are used as therapeutic monoclonal antibodies incorporate those portions of the constant region of an antibody necessary to evoke a therapeutically useful immunological response in the subject being treated.

Therapeutic monoclonal antibodies may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

C. Subjects

The method disclosed herein may be employed with subjects suspected of having solid or cystic tumors residing in the central nervous system, particularly the brain (e.g., in the cerebellum, or more preferably in the cerebral cortex, including the frontal, parietal, occipital and temporal lobes). In addition, the method disclosed herein may be employed with solid tumors residing in other solid tissue organs, such as liver, kidney, spleen, brain, breast, muscle, and prostate.

The tumor may be any tumor, primary or secondary, that expresses tenascin, including (but not limited to) astrocytic tumors, melanomas, breast carcinomas, and Wilm's tumor.

The term "astrocytic tumors" as used herein is used in accordance with the World Health Organization Classification Scheme, and includes astrocytomas, anaplastic astrocytomas, and glioblastoma multiforme. See also D. Russell and L. Rubinstein, *Pathology of Tumors of the Nervous System*, pp. 83–289 (1989) (Williams and Wilkins).

Some tumors which may be treated by the method of the present invention are cystic tumors: that is, tumors which grow around a fluid-filled cavity, or cyst. Examples of such cystic tumors include (but are not limited to) cystic astrocytic tumors such as cystic astrocytomas, cystic anaplastic astrocytomas, and cystic glioblastoma multiforme.

For administration, the antibody will generally be mixed, prior to administration, with a non-toxic, pharmaceutically acceptable carrier substance (e.g. normal saline or phosphate-buffered saline), and will be administered using any medically appropriate procedure, e.g., intravenous or intra-arterial administration, injection into the cerebrospinal fluid). In certain cases, intradermal, intracavity, intrathecal or direct administration to the tumor or to an artery supplying the tumor is advantageous. In addition, either intrathecal administration or injection into the carotid artery are advantageous for therapy of tumors located in the brain.

Dosage of the antibody will depend, among other things, on the tumor being treated, the route of administration, the nature of the therapeutic agent employed, and the sensitivity of the tumor to the particular therapeutic agent. For example, the dosage will typically be about 1 to 10 micrograms per Kilogram subject body weight. In another example, where the therapeutic agent is $^{131}I$, the dosage to the patient will typically be from 10 mCi to 100, 300 or even 500 mCi. Stated otherwise, where the therapeutic agent is $^{131}I$, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}I$. The antibody can be administered to the subject in a series of more than one administration, and regular periodic administration will sometimes be required.

The antibody may be administered by depositing it into the inner cavity of a cystic tumor (i.e., a fluid-filled cavity around which the tumor grows) by any suitable technique, such as by direct injection (aided by stereotaxic positioning of an injection syringe, if necessary) or by placing the tip of an Ommaya reservoir into the cavity and administering the antibody through the Ommaya reservoir. The Ommaya reservoir apparatus is known. See, e.g., F. Balis and D. Poplack, *Am J. Pediatr. Hematol. Oncol.* 11, 74, 76 FIG. 1 (1989). Where the tumor is a solid tumor, the antibody may be administered by first creating a resection cavity in the location of the tumor in the manner described below, and then depositing the antibody in the resection cavity in like manner as with cystic tumors.

D. Surgical Creation of an Intracranial Cystic Resection Cavity

Virtually all cortical solitary metastases, including those appearing in the four cerebral lobes (frontal, parietal, temporal and occipital) and in the cerebellum, are amenable to creation of the cystic resection cavities by surgery, particularly those in the cerebral lobes.

The procedure differs from an ordinary craniotomy and tumor resection in only a few minor respects. First, the smallest possible cortical incision is made and the tumor is removed to the greatest extent possible by resection of tissue within the small cortical incision and in the depths of the cortex. A so-called gross total tumor resection is attempted, with the only thing prohibiting gross total resection being the potential impingement upon neurologically active areas such as speech or motor areas that would leave permanent neurologic damage if surgically approached. Following gross total resection of the tumor in a standard neurosurgical fashion with cauterization, suction, and forceps removal, the cavity is then preferably rinsed with saline until all bleeding is stopped by cauterization. Next, the pia-arachnoid membrane, which is the surface membrane lining the brain around the cortical incision, is preferably cauterized to enhance the formation of fibroblastic reaction and scarring in the pia-arachnoid area and any astroglial scarring in the areas of normal brain. The result is the formation of an enclosed, fluid-filled cavity within the brain tissue at the location from which the tumor was removed (i.e., the cavity is surrounded on all sides by the organ tissue). The enclosed nature of the resection cavity enhances retention and localization of the therapeutic agent to be administered at the desired site. If desired for administering the therapeutic agent, an Ommaya reservoir may then be placed into the cavity with the tip of the catheter as deep as possible in the tumor bed, and the reservoir secured to the bone in accordance with standard techniques. A standard water-tight dural closure may then be carried out with sutures, as in any other craniotomy.

Resection cavities are formed in other solid tissue organs, as described above, by modification of the foregoing techniques which will be apparent to those skilled in the art.

The present invention is explained in greater detail in the following non-limiting Examples.

COMPARATIVE EXAMPLE A

Survival of Glioblastoma Multiforme Patients

The survival of 383 human glioblastoma multiforme patients treated by the best available techniques is given in FIG. 1 as line 1. The proportion of the total population surviving after diagnosis (diagnosis occuring on year 0.0) is indicated. Note that the line drops precipitously, indicating the relentless and aggressive nature of this disease.

EXAMPLE 1

Drug Formulation

Drug is formulated as 2 ml of a sterile, pyrogen-free solution that contains 10 mg of monoclonal antibody 81C6 (20–60 mCi iodine-131), 0.7 to 0.9% sodium chloride, 0–0.6% sodium phosphate, 0.5% albutein, and water. Antibody is conjugated to iodine-131 by the Iodogen method in accordance with known techniques (see, e.g., R. Moseley et al., *Br. J. Cancer* 62, 637 (1990)) and the drug formulation is prepared within 24 hours of administration to the patient.

EXAMPLE 2

Intracystic Administration of 81C6 to a Recurrent Cystic Glioblastoma Patient

A 45 year old adult male with a recurrent cystic glioblastoma was administered 15.2 mCi of $^{131}$I conjugated to 10 mg of monoclonal antibody 81C6 by the Iodogen method and formulated as described above through an Ommaya reservoir placed into the recurrent tumor cyst. Clinical and radiographic examination after treatment indicated a complete response.

The patient received a second treatment of the administration of 20.0 mCi of $^{131}$I conjugated to 7.9 mg of monoclonal antibody 81C6 by the ATE method and formulated as described above through the Ommaya reservoir approximately 15 months after the first treatment.

As of 18 months from the first treatment, the patient remained alive. This patient is indicated as line 2 in FIG. 1.

EXAMPLE 3

Intracystic Administration of 81C6 to a Recurrent Cystic Astrocytoma Patient

A 29 year old adult female with a recurrent cystic astrocytoma was administered 21.7 mCi of $^{131}$I conjugated to 10 mg of monoclonal antibody 81C6 by the Iodogen method through an Ommaya reservoir placed into the recurrent tumor cyst. Clinical and radiographic examination after treatment indicated a partial response. The patient was still alive 11 months after treatment. This patient is indicated as line 3 in FIG. 1.

EXAMPLE 4

Intracystic Administration of 81C6 to a Recurrent Cystic Glioblastoma Patient

A 14 year old female with a recurrent cystic glioblastoma was administered 20.07 mCi of $^{131}$I conjugated to 10 mg of monoclonal antibody 81C6 by the Iodogen method through an Ommaya reservoir placed into the recurrent tumor cyst. Clinical and radiographic examination after treatment indicated progressive disease. The patient survived 4 months beyond treatment. This patient is indicated as line 4 in FIG. 1.

EXAMPLE 5

Surgical Creation of an Intracranial Cystic Resection Cavity in a Human Glioblastoma Patient A cystic resection cavity was surgically created in a 53 year old female patient afflicted with an intracranial glioblastoma. The procedure was carried out in essentially the same manner as an ordinary craniotomy and tumor resection, but differed in a few respects. First, the smallest possible cortical incision was made and the tumor was removed to the greatest extent possible by resection of tissue within the small cortical incision and in the depths of the cortex. A so-called gross total tumor resection was attempted, with the only thing prohibiting gross total resection being the potential impingement upon neurologically active areas such as speech or motor areas that would leave permanent neurologic damage if surgically approached. Following gross total resection of the tumor in a standard neurosurgical fashion with cauterization, suction, and forceps removal, the cavity was then rinsed with saline until all bleeding was stopped by cauterization and the pia-arachnoid membrane, which is the surface membrane lining the brain around the cortical incision, was cauterized to enhance the formation of fibroblastic reaction and scarring in the pia-arachnoid area and any astroglial scarring in the areas of normal brain. An Ommaya reservoir was then placed into the cavity with the tip of the catheter as deep as possible in the tumor bed, and the reservoir secured to the bone in accordance with standard techniques. A standard water-tight dural closure was then carried out with sutures.

EXAMPLE 6

Administration of 81C6 to an Intracranial Cystic Resection Cavity in a Human Glioblastoma Patient The patient described in the preceding example was administered 15.0 mCi of $^{131}$I conjugated to 10 mg of monoclonal antibody 81C6 by the Iodogen method through an Ommaya reservoir placed into the cystic resection cavity created as described above. Three months after administration, the patient was still alive.

Technetium albumin injections of the cystic resection cavity, followed by sequential radionuclide scans of the brain, showed up to approximately 90% retention of the injected radionuclide albumin conjugate for 72 hours after injection and significant retention of the therapeutic dose of radiolabeled antibody to give a radiation dose calculated to range between 20,000 and 60,000 rads to the walls of the cyst.

EXAMPLE 7

Cloning and Expression of a Mouse/human Chimeric Antibody Cross-reactive with 81C6

This example describes the molecular cloning and characterization of variable region genes for 81C6 antibody. The mouse/human chimeric genes were transfected into SP2/0 cells, and stable integration and expression was obtained. The production of chimeric 81C6 antibody was two to six times higher than that of the parent mouse 81C6 antibody. These data clearly demonstrate that a high level of chimeric antibody production depends upon multiple copies of gene integration and strong expression of both light-chain (SEQUENCE ID NO. 3) and heavy-chain (SEQ ID NO: 1) chimetic genes in the same transfectoma.

I. MATERIALS AND METHODS

Cells and Cell Culture

Native 81C6 (n81C6) antibody has been generated and characterized previously (M. Bourdon et al., *Cancer Res.* 43, 2796, (1983)). The SP2/0 cell line was obtained from the American Type Cell Collection (Rockville, Md.). Cells were grown in 1 × zinc option medium (GIBCO, Grand Island, N.Y.) containing 10% fetal bovine serum (GIBCO).

Purification and Analysis of RNA and DNA

Total RNA and genomic DNA were isolated from cells using the guanidine isothiocyanate cushion method of ultracentrifugation (J. Chirgwin et al., *Biochemistry* 18, 5294 (1979)) as detailed in S. Batra et al., *Cel. Growth Differ.* 2, 385 (1991) and S. Batra et al., *J. Biol. Chem.* 266, 6830 (1991). Genomic DNA was further purified by sodium dodecyl sulfate-protenase-K digestion and phenol:chloroform (1:1, v/v) extraction. The RNA pellet was resuspended in 0.3M sodium acetate and precipitated with ethanol. Plasmid DNA was isolated by alkaline lysis and PZ523 columns (5 prime→3 prime, Boulder, Colo.). DNA was analyzed using standard Southern blotting. After digestion with various restriction endonucleases, DNA fragments were fractionated through 0.8% agarose gel by electrophoresis and transferred to a nitrocellulose or nylon transfer membrane (Scheicher & Schuell, Keene, N.H.). The membrane was then hybridized with [$^{32}$P]dCTP (ICN Biochemicals, Irvine, Calif.)—labeled DNA probes to identify the immunoglobulin gene. The heavy and light chains were detected with pJH-11 and pJK probes, respectively. The pJH-11 probe is a 1.9-kilobase (kb) BamHI-EcoRI fragment of a murine heavy-chain gene that includes the J3 and J4 segments and the enhancer region, and the pJK probe is a 2.7-kb HindIII DNA fragment of a murine K-light-chain gene containing J1–5 segments.

Total RNA from control and transfected cells was fractionated by electrophoresis on a formaldehyde-containing agarose gel and then transferred to nylon membrane under conditions recommended by the supplier (Scheicher & Schuell). The heavy-chain transcription was detected using an 81C6 heavy-chain-specific 6-kb EcoRI fragment as the probe. The light-chain transcript was defined using an 81C6 light-chain-specific 11-kb HindIII fragment as the probe.

Antibody Purification and Amino Acid Sequence Analysis

Both native 81C6 (n81C6) and chimeric 81C6 (ch81C6) were purified from cultured supernatants or athymic mouse ascites using protein A-Sepharose (Pharmacia, Piscataway, N.J.) chromatography. The amino acid sequence of each chain of both the antibodies (normal and chimeric) was analyzed by automated Edman degradation in an Applied Biosystems (Foster City, Calif.) Model 477A sequencer. On-line phenylthiohydantoin analysis was employed in conjunction with an Applied Biosystems Model 120A high-performance liquid chromatography apparatus (J. Enghild et al., *J. Biol. Chem.* 266, 747 (1991).

Construction and Screening of Genomic Libraries

81C6 Heavy-chain and light-chain libraries were constructed from size-selected DNA restriction fragments that had been identified as containing putative rearranged variable region genes by Southern blot analysis. For the heavy-chain libraries, genomic DNA was digested with EcoRI and fractionated through agarose gel. The 3- and 6-kb fragments were isolated from agarose gel using the Genclean II kit (Bio 101, Inc., La Jolla, Calif.) and then ligated separately into the EcoRI site of the λ-ZAP II vector (Stratagene, La Jolla, Calif.). For the light-chain library, 81C6 DNA was digested with HindIII, and the 11-kb fragment was cloned into the HindIII site of the λ-DASH vector (Stratagene). The packaging reaction was performed in vitro using Gigapack gold packaging extracts according to the manufacturer's instructions (Stratagene). The libraries were screened with pJH-11 for heavy chains and pJK for light chains. The positive clones were rescued or subcloned and further characterized by DNA sequencing using -oligonucleotide primers that are specific for the $_\gamma$-heavy-chain and $_\kappa$-light-chain J-regions and Sequenase Version 2.0 (United States Biochemical, Cleveland, Ohio).

Double-strand sequencing was employed for sequence analysis, and both sense and antisense strands of DNA were sequenced. Heavy chain-specific primers were synthesized by Biosynthesis (Denton, Tex.) for each heavy-chain J-region as follows: J1 (5'-CCCGTTTCAGAATGGAATGTGCAG-3') (SEQ ID NO. 5), J2 (5'-CTAAGCTGAATAGAAGAGAGAGG-3') (SEQ ID NO. 6), J3 (5"-TGGGAGAAGTTAGGACT-3'), (SEQ ID NO. 7), and J4 (5'-ATAAAGACCTGGAGAGGCC-3'), (SEQ ID NO. 8), $_\gamma$-Chain J-region primers were made by Biosynthesis as described by Hoogenboom, et al., 1990. To complete the 5' terminal sequence and to read the opposite strand, internal 81C8-specific primers were also used. The amino acid sequence was translated from the nucleotide sequence and compared with the actual sequence.

Construction of Chimeric Vectors

The functional, rearranged 81C6 heavy-chain variable region gene was inserted into expression vector pSV2ΔHgpt-HuG2, which contains a genomic fragment encoding the human IgG2-constant region and the Ecogpt gene providing resistance to mycophenolic acid. The 81C6 light-chain variable region gene was ligated into expression vector pSV184ΔHneo-HuK, which includes a DNA fragment encoding the human K-constant region and the neogene giving resistance to G418 (V. Oi and S. Morrison, *Biotechniques* 4, 214 (1986).

Transfection

The chimeric heavy-chain and light-chain constructs were separately introduced or cotransfected into SP2/0 cells using a lipofectin reagent (GIBCO/BRL). The transfected cells were incubated at 37° C. in a 5% CO2 atmosphere in 1 × zinc option medium for 24 hours and then in medium containing 10% fetal bovine serum. After 48-h incubation, the cells were transferred to a 96-well microtiter plate and grown in selection medium containing G418 and/or mycophenolic acid. The supernatants of drug-resistant cells were screened for anti-tenascin activity by enzyme-linked immunosorbent assay.

Immunoassay for Anti-tenascin Activity

Each microtiter well (Dynatech Laboratories, Inc, Chantilly, Va.) was coated with 50 μl of 2 mg/μl human intact tenascin or recombinant tenascin fragment in 0.1M sodium carbonate buffer (pH 9.6) overnight at 4° C., washed with 0.025% gelatin, 0.1% BRIJ 35 (Sigma, St. Louis, Mont.) in 115 mM sodium phosphate buffer (pH 7.4) 3 times, and blocked with the washing buffer for 30 min. After the washing buffer was removed, 50 μl of culture supernatant or purified antibody was added to each well and the contents were incubated for 1 h at room temperature, washed, and incubated with 50 μl of biotinylated goat anti-mouse (for mouse antibody) or goat anti-human (for chimeric antibody) IgG (BRL) for 1 h at room temperature. The plates were washed and incubated with 50 μl of streptavidin-alkaline phosphatase (BRL) for 1 h at room temperature, rewashed, and then incubated with 100 μl/per well of phosphatase substrate (Sigma) (4 mg/ml in 10%) diethanolamine, 0.5 mM $MgCl_2$). The reaction was stopped with 10mM L-cysteine, and absorbance was read at 405 nm.

Radioiodination

Purified n81C6 and ch81C6 (IgG2) were labeled with $^{125}I$ (Amersham, Arlington Heights, Ill.) using the Iodo-Gen (Pierce, Rockford, Ill.) in accordance with known techniques (P. Fraker and J. Speck, *Biochem. Biophys. Res. Commun.* 80, 849 (1978)). The labeled antibodies were separated from free radioiodine by passage through a Sephadex G-25 column. Iodinated antibody preparations were greater than 97% in trichloroacetic acid precipitation analysis. The size and homogeneity of radiolabeled antibody were monitored by size exclusion high-performance liquid chromatography in conjunction with a Model 170 flow-through gamma detector (Beckman, Irvine, Calif.).

Immunoreactivity and Affinity Determination

For the immunoreactivity assay, 50 ng of labeled antibody was incubated overnight in duplicate with different amounts of D-54 MG human glioma xenograft (antigen positive) and normal rat liver (antigen negative) homogenate in 1 ml of 115 mM phosphate buffer containing 1% bovine serum albumin. The specific binding percentage was calculated by subtracting the percentage bound to the rat liver homogenate from that bound to the D-54 tumor homogenate.

A modified Scatchard analysis was used to measure the binding affinity of labeled ch81C6. Serially diluted 125I-labeled antibody (200 μl, 1:2 dilution starting from 1600 ng/ml) was incubated in 48-well plates overnight at 37° C. with the antigen-positive human glioma cell line U-251 MG-C3 fixed in glutaraldehyde and the antigen-negative human osteogenic sarcoma cell line 2T. The cells were washed and solubilized with 2N NaOH, and the radioactivity was measured with a gamma counter. The data was analyzed in accordance with known techniques (Y. S. Lee et al., *Cancer Res.* 48, 559 (1988)).

Cross-competition Assay

Serially diluted (1:2 dilution starting from 100 μg/well in 50 μl) and unlabeled antibodies, experimental or control, were added to glutaraldehyde-fixed U-251 MG-C3 and 2T cells in 96-well plates. After the cells were incubated at 37° C. for 2 h, 50 μl of $^{125}I$ n81C6 or 125I ch81C6 (IgG2) (200,000 cpm) were added to each well, and the plates were incubated at 37° C. for 2 h. The cells were washed and solubilized with 2N NaOH, and the bound reactivity was counted with a gamma counter. The percentage binding was determined by the formula:

$$\frac{\text{cpm }^{125}I\text{ antibody bound following unlabled antibody incubation in positive cells}}{\text{cpm }^{125}I\text{ antibody bound following buffer incubation in positive cells}}$$

Each value was corrected for counter background and cpm bound in antigen negative cell.

II. RESULTS

Identification and Cloning of Rearranged 81C6 Variable Region Genes

Genomic DNA from a 81C6 hybridoma; its fusion partner, myeloma P3X63/Ag8.653; and BALB/c mouse liver representative of the mouse germ line were digested with EcoRI, HindIII and BamHI and subjected to the Southern blot analysis to identify the putative rearranged 81C6 variable region genes. The hybridization pattern using the $^{32}P$-labeled heavy-chain probe pJH-11 revealed that the 3- and 6-kb EcoRI bands, a 1.2-kb HindIII band, and a 11-kb BamH1 band were unique to the 81C6 hybridoma. These unique bands were considered as the putative rearranged heavy-chain variable region genes. Hybridization using the $^{32}P$-labeled light-chain probe pJK revealed an 11-kb HindIII band and a 6-kb BamHI band which were found in the 81C6 hybridoma only, and which were most likely the putative rearranged light-chain variable region genes.

In order to clone the heavy-chain gene, two genomic libraries were constructed for 3- and 6-kb EcoRI DNA fragments and screened with the mouse heavy-chain probe pJH-11. Positive clones were subjected to nucleotide sequencing. The sequence analysis found that the clone isolated from a 3-kb fragment library was an aberrantly rearranged gene. The nucleotide sequence of a positive clone from a 6-kb fragment library is shown in FIG. 2A. It had all the features of an intact variable region, including a functional leader sequence, in-frame V-D and D-J junctions, and cysteines 22 and 92, which are necessary for an intrachain disulfide bond. The conserved octanucleotide, ATGCAAAT, was found at nucleotide 144, upstream from the 3' end of the first exon. The 81C6 heavy-chain variable region segment was found to rearrange to the J3 segment. The N-terminal amino acid sequence matched the deduced amino acid sequence.

The putative K-chain variable region of the 11-kb HindIII DNA fragment was isolated from the genomic library prepared in the λ-DASH vector using the light-chain probe pJK. FIG. 2B shows the nucleotide sequence for the 81C6 K-chain, which is rearranged to the J1 segment. The conserved octanucleotide, ATTTGCAT, was found at nucleotide 147, upstream from the 3' end of the first exon. A large 358-base pair intervening sequence was found in the middle of the leader peptide. The deduced amino acid sequence matched the partial sequence obtained using N-terminal sequencing of the purified 81C6 antibody.

Construction and Transfection of Chimeric Genes

The 6-kb EcoRI fragment of the cloned 81C6 heavy-chain variable region gene was ligated at the unique EcoRI site in the intron before the first exon in the human IgG2 constant region of the expression vector pSV2ΔHgpt-HuG2. Similarly, the 11-kb HindIII fragment of the cloned 81C6 light-chain variable region gene was inserted into a unique HindIII site in expression vector pSV184ΔHneo-HuK, which contained the human K-constant region gene. The chimeric heavy-chain and light-chain constructs were either separately introduced into SP2/0 cells for confirming the orientation of 81C6 variable region genes in the expression vector, or cotransfected into the SP2/0 cells for expressing chimeric antibody. The transfected cells were grown in medium containing G418 and/or mycophenolic acid. Supernatants of cells resistant to both drugs were screened for the presence of antibody activity using human intact tenascin-coated plates and enzyme-linked immunosorbent assay. Thirteen positive transfectomas were obtained from three transfection experiments. Five of them were subcloned twice, expanded in culture, and injected into athymic mice for producing antibody.

Expression of ch81C6

Genomic DNA was isolated from the transfected and control cells and analyzed by Southern blotting to determine the integration of chimeric constructs into the SP2/0 cell genome (data not shown). Hybridization bands at 3, 6, and 6.5 kb were found in n81C6. All untransfected and transfected SP2/0 cells showed both a strong 6-kb and a weak 3.4-kb band, which were considered to be endogenous immunoglobulin genes from the SP2/0 genome. The hybridization signal in SP2/0 cells transfected with the heavy-chain expression vector was identical to that of untransfected SP2/0 cells. Additional hybridization bands of different sizes were found in cells transfected with the heavy-chain construct alone or in transfectomas that received both heavy- and light-chain chimeric constructs and secreted chimeric antibody. An exception was transfectomas H3D4A10 and F12D9A2, which showed additional hybridization bands only after digestion with HindIII or BamHI. The strongest integration signal, with additional, intense bands, was found in transfectoma F9C11A5.

The hybridization of the light-chain probe to the HindIII-digested DNA blot showed hybridization bands at 11 and 2.5 kb in n81C6 as expected (data not shown). Hybridization bands at 6.5 and 2.5 kb were shown in all untransfected and transfected SP2/0 cells; these two bands were considered to be endogenous immunoglobulin genes from the SP2/0 genome. The hybridization pattern of transfected cells with the vector alone was the same as the pattern of untransfected SP2/0 cells. Additional hybridization bands of different sizes were also detected in all transfected cells either with the light-chain chimeric construct alone or with both light- and heavy-chain chimeric constructs. These additional bands most likely resulted from the integration of chimeric DNA constructs into the genome. Lanes 4 and 5 show transfected cells with the light-chain chimeric construct alone. The DNA integration signals varied with different transfectomas. The strongest signal here, as with the heavy-chain probe, was also found in transfectoma F9C11A5.

Total RNA, purified from the transfected and control cell lines, was separated by agarose/formaldehyde gel electrophoresis, Northern blotted, and probed with a 6-kb heavy-chain variable segment and an 11-kb HindIII DNA fragment of 81C6 for heavy-chain and light-chain gene expression, respectively. The data showed the expression of heavy-chain mRNA in the untransfected and transfected cells. The same blot was probed with β-actin cDNA as a control for mRNA quantity and quality (P. Gunning et al., Mol. Cel. Biol. 3, 787 (1983)). The heavy-chain mRNA was detected in n81C6, transfected SP2/0 cells with the expression vector containing the 81C6 heavy chain in sense orientation, and in all transfectomas secreting chimeric 81C6. But no signal was found in untransfected SP2/0 cells, transfected cells with expression vector alone, or transfected cells with the expression vector carrying the 81C6 heavy chain in antisense orientation. Light-chain mRNA was detected in n81C6, transfected SP2/0 cells with the expression vector containing the 81C6 light-chain variable region gene (SEQ ID NO. 3) in sense orientation, and all transfectomas secreting chimeric antibody. There was no hybridization signal found in untransfected SP2/0, transfected cells with the light-chain expression vector alone, and in cells with the expression vector containing the 81C6 light chain in antisense orientation. Strong expression signals of both heavy- and light-chain mRNA were detected in the transfectoma F9C11A5.

Chimeric 81C6 antibody was purified from cultured supernatants and ascites by protein A-Sepharose chromatography. The production levels of five transfectomas in supernatant and in ascites are presented in Table 1. High antibody production was obtained from the supernatants and ascites of transfectoma F9C11A5, which had multiple copies of integration of heavy- and light-chain chimeric constructs and high levels of heavy- and light-chain mRNA expression. The antibody concentration in transfectoma F9C11A5 ascites was two to six times higher than that of n81C6, which was 2.5 mg/ml ascites in previous purification. Production levels of the four other transfectomas were similar, with the exception of H3D4A10 ascites, which was unusually low.

TABLE 1

| Antibody production by ch81C6 transfectomas and n81C6. | | |
|---|---|---|
| Cells | Antibody in supernatant (ug/ml) | Antibody in ascites (mg/ml) |
| ch81C6 transfectomas | | |
| F9C11A5[a] | 31.4 | 6.5 |
| G4D10A12.5 | 3.7 | 2.5 |
| B4D9B1 | 4.4 | 1.9 |
| H3D4A10 | 4.7 | 0.09 |
| F12D9A2 | 3.4 | 1.5 |
| n81C6 | 8.5 | 2.5 |

[a]F9C11A5 transfectoma was further used for production of ch81C6 antibodies, which showed a varied yield of 65 to 13.9 mg/ml of ascites.

Characterization of ch81C6

The ch81C6 from high production transfectoma F9C11A5 was purified and further characterized. It was labeled with $^{125}$I using the Iodogen method, and the percentage of immunoreactivity was determined by absorption with D-54 MG xenograft homogenate. The affinity constant was defined by Scatchard analysis using binding assay on a tenascin-expressing cell line U-251 MGC-3 as described above. Immunoreactivity of 58% was obtained for $^{125}$I ch81C6, which was comparable to a range of 35–70% for $^{125}$I n81C6 in previous experiments (Y. S. Lee et al., Cancer Res. 48, 559 (1988); Y. S. Lee et al., Cancer Res. 48, 2904

(1988)). The binding affinity of $^{125}$I ch81C6 was $1.67 \times 10^8$ M$^{-1}$, which was also in the range of $3.3 \times 10^7$ to $3.0 \times 10^8$ M$^1$ for radiolabeled n81C6 in previous reports (Lee et al., supra).

Cross-competition assays were performed on U-251 MG-C3 cells using $^{125}$I ch81C6 and $^{125}$I n81C6 to determine their binding properties. Less than 10% $^{125}$I ch81C6 binding activity was detected after incubation with unlabeled n81C6 or unlabeled ch81C6. The negative control chimeric IgG2, TPS3.2, did not show significant inhibition. Similar reciprocal inhibition of binding was observed for $^{125}$I n81C6 with unlabeled ch81C6 or unlabeled n81C6, but not with negative control murine IgG2b 45.6.

We also tested the immunoreactivity of 81C6 with four recombinant tenascin fragments containing fibronectin III domains 3–5, 6–12, 13–15, and epidermal growth factor-like domains, respectively. Both native and chimeric 81C6 reacted with tenascin fragments containing fibronectin III domains 6–12 as expected, but not with other fragments tested.

The foregoing examples are illustrative of the present invention, and are not to be construed as limiting thereof. The invention is defined by the following claims, with equivalents of the claims to be included therein.

---

That which is claimed is:

1. A method of treating a cystic brain tumor which expresses tenascin, comprising:
administering to a human subject afflicted with a cystic brain tumor expressing tenascin an antibody that binds to tenascin in a therapeutically effective amount,
wherein said administering step is carried out by depositing said antibody in the cyst cavity of said cystic brain tumor,
wherein said antibody is coupled to a radioisotope, and
wherein said antibody is selected from the group consisting of monoclonal antibody 81C6 and antibodies that bind to the epitope bound by monoclonal antibody 81C6.

2. A method according to claim 1, wherein said tumor is an astrocytic tumor.

3. A method according to claim 1, which tumor is selected from the group consisting of cystic astrocytomas and cystic anaplastic astrocytomas.

4. A method according to claim 1, which tumor is a cystic glioblastoma multiforme.

5. A method according to claim 1 wherein said radioisotope is selected from the group consisting of $^{131}$I, $^{90}$Y, $^{211}$At, $^{212}$Bi, $^{67}$Cu, $^{186}$Re, $^{188}$Re, and $^{212}$Pb.

6. A method according to claim 1, wherein said radioisotope is $^{131}$I.

7. A method according to claim 1, wherein said antibody coupled to a radioisotope is administered in an amount of from 5,000 rads to 100,000 rads.

8. A method of treating a cystic astrocytic brain tumor which expresses tenascin, comprising:
administering to a human subject afflicted with a cystic astrocytic brain tumor expressing tenascin the antibody 81C6 conjugated to $^{131}$I in a therapeutically effective amount,
wherein said administering step is carried out by depositing said antibody in the cyst cavity of said cystic brain tumor.

9. A method according to claim 8, which tumor is selected from the group consisting of cystic astrocytomas and cystic anaplastic astrocytomas.

10. A method according to claim 8, which tumor is a cystic glioblastoma multiforme.

11. A method according to claim 8, wherein said antibody coupled to $^{131}$I is administered in an amount of from 5,000 rads to 100,000 rads.

12. A method according to claim 8, wherein said administering step is carried out by injection.

13. A method of treating a solid brain tumor which expresses tenascin, in a human subject in need of such treatment, comprising:

removing a solid brain tumor expressing tenascin from an afflicted human subject; then forming an enclosed resection cavity at the location from which said solid brain tumor was removed, and then administering to said subject an antibody that binds to tenascin in a therapeutically effective amount, wherein said administering step is carried out by depositing said antibody in said resection cavity, wherein said antibody is coupled to a radioisotope, and wherein said antibody is selected from the group consisting of monoclonal antibody 81C6 and antibodies that bind to the epitope bound by monoclonal antibody 81C6.

14. A method according to claim 13, wherein said tumor is an astrocytic tumor.

15. A method according to claim 13 wherein said radioisotope is selected from the group consisting of $^{131}$I, $^{90}$Y, $^{211}$At, $^{212}$Bi, $^{67}$Cu, $^{186}$Re, $^{188}$Re, and $^{212}$Pb.

16. A method according to claim 13, wherein said radioisotope is $^{131}$I.

17. A method according to claim 13, wherein said antibody coupled to a radioisotope is administered in an amount of from 5,000 rads to 100,000 rads.

18. A method according to claim 13, wherein said administering step is carried out by injection.

19. A method of treating a solid astrocytic tumor which expresses tenascin in the brain of a human subject in need of such treatment, comprising:

removing a solid astrocytic tumor expressing tenascin from the brain of an afflicted human subject; then forming an enclosed resection cavity in the brain of said subject at the location from which said solid tumor was removed; and then administering to said subject antibody 81C6 coupled to $^{131}$I in a therapeutically effective amount, wherein said administering step is carried out by depositing said antibody in said resection cavity.

20. A method according to claim 19 wherein said antibody is administered in an amount of from 5,000 rads to 100,000 rads.

21. A method according to claim 19, wherein said administering step is carried out by injection.

* * * * *

UNITED STATES PATENT AND TRADEMARK OFFICE
CERTIFICATE OF CORRECTION

PATENT NO. : 5,624,659
DATED : April 29, 1997
INVENTOR(S) : Bigner et al.

It is certified that error appears in the above-indentified patent and that said Letters Patent is hereby corrected as shown below:

Col. 8, line 57, replace "$\gamma$" with --$k$--.

Signed and Sealed this

Fifth Day of August, 1997

Attest:

Attesting Officer

BRUCE LEHMAN
Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 660 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(149..193, 277..642)

( x i ) SEQUENCE DESCRIPTION: SEQ ID NO:1:

```
CTGGACTAGG TTCTTATGTA AGAAGTCCCC TGCTCATCAT TATGCAAATT ACCTGAGTCT        60

ATGGTGATTA AAACAGGGAT GTCCACACCC TTAAATCAAC CGACGATCAG TGTCCTCTCC       120

AAAGTCCCTG AACACACTGA CTCTAACC ATG GAA TGG AGT TGG ATA TTT CTC          172
                                Met Glu Trp Ser Trp Ile Phe Leu
                                 1               5

TTT CTC CTG TCA GGA ACT GCA GGTAAGGGGC TCACCAGTTC AAAATCTGAA            223
Phe Leu Leu Ser Gly Thr Ala
         10              15

GTGGAGACAG GACCTGAGGT GACAATGACA TCTACTCTGA CATTCTCTCC TCA GGT          279
                                                             Gly

GTC CAC TCT GAG GTC CAG CTG CAG CAG TCT GGA CCT GAG CTG GTA AAG        327
Val His Ser Glu Val Gln Leu Gln Gln Ser Gly Pro Glu Leu Val Lys
             20              25                   30

CCT GGG GCT TCA GTG AAG ATG TCC TGC AAG GCT TCT GGA TAC ACA TTC        375
Pro Gly Ala Ser Val Lys Met Ser Cys Lys Ala Ser Gly Tyr Thr Phe
         35                  40                  45

ACT AGC TAT GTT GTG CAC TGG GTG AAG CAG AAC CCT GGG CAG GGC CTT        423
Thr Ser Tyr Val Val His Trp Val Lys Gln Asn Pro Gly Gln Gly Leu
     50                  55                  60

GAG TGG ATT GGA TAT ATT AAT CCT TTC AAT GAT GGT ACT AAG TAC AAT        471
Glu Trp Ile Gly Tyr Ile Asn Pro Phe Asn Asp Gly Thr Lys Tyr Asn
 65                  70                  75                  80

GAG AAC TTC AAA GGC AAG GCC ACA CTG ACT TCA GAC AGA TCC TCC AGC        519
Glu Asn Phe Lys Gly Lys Ala Thr Leu Thr Ser Asp Arg Ser Ser Ser
                 85                  90                  95

ACA GCC TAC ATG GAG CTC AGC AGC CTG ACC TCT GAG GAA TCT GCG GTC        567
Thr Ala Tyr Met Glu Leu Ser Ser Leu Thr Ser Glu Glu Ser Ala Val
```

```
                         100                      105                          110
TAT  TTC  TGT  GCA  AGA  GAC  ATG  GGT  CGC  GAA  GGC  TTT  GCT  TAC  TGG  GGC       615
Tyr  Phe  Cys  Ala  Arg  Asp  Met  Gly  Arg  Glu  Gly  Phe  Ala  Tyr  Trp  Gly
               115                      120                      125

CAA  GGG  ACT  CTG  GTC  ACT  GTC  TCT  GCA  GGTGAGTCCT  AACTTCTC                    660
Gln  Gly  Thr  Leu  Val  Thr  Val  Ser  Ala
     130                      135
```

( 2 ) INFORMATION FOR SEQ ID NO:2:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Trp  Ser  Trp  Ile  Phe  Leu  Phe  Leu  Leu  Ser  Gly  Thr  Ala  Gly
 1              5                        10                       15

Val  His  Ser  Glu  Val  Gln  Leu  Gln  Gln  Ser  Gly  Pro  Glu  Leu  Val  Lys
               20                        25                       30

Pro  Gly  Ala  Ser  Val  Lys  Met  Ser  Cys  Lys  Ala  Ser  Gly  Tyr  Thr  Phe
          35                        40                       45

Thr  Ser  Tyr  Val  Val  His  Trp  Val  Lys  Gln  Asn  Pro  Gly  Gln  Gly  Leu
     50                        55                       60

Glu  Trp  Ile  Gly  Tyr  Ile  Asn  Pro  Phe  Asn  Asp  Gly  Thr  Lys  Tyr  Asn
65                        70                       75                        80

Glu  Asn  Phe  Lys  Gly  Lys  Ala  Thr  Leu  Thr  Ser  Asp  Arg  Ser  Ser  Ser
               85                        90                       95

Thr  Ala  Tyr  Met  Glu  Leu  Ser  Ser  Leu  Thr  Ser  Glu  Glu  Ser  Ala  Val
          100                       105                      110

Tyr  Phe  Cys  Ala  Arg  Asp  Met  Gly  Arg  Glu  Gly  Phe  Ala  Tyr  Trp  Gly
     115                       120                      125

Gln  Gly  Thr  Leu  Val  Thr  Val  Ser  Ala
     130                       135
```

( 2 ) INFORMATION FOR SEQ ID NO:3:

( i ) SEQUENCE CHARACTERISTICS:
        ( A ) LENGTH: 882 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: join(121..168, 527..874)

( x i ) SEQUENCE DESCRIPTION: SEQ ID NO:3:

```
TATCAACCAG  GAGATTTGCA  TATTGCTCCC  TAGGGAGGAC  CTCTTCTTGC  AGGTGCAGGG        60

TAAAAGCTCA  CTCCTCTTTC  TGTCTTGATT  ACTTTGACT  CACCATATCA  AGTTCGCAGA        120

ATG  AGG  TTC  TCT  GCT  CAG  CTT  CTG  GGG  CTG  CTT  GTG  CTC  TGG  ATC  CCT        168
Met  Arg  Phe  Ser  Ala  Gln  Leu  Leu  Gly  Leu  Leu  Val  Leu  Trp  Ile  Pro
 1              5                        10                       15

GGTAAGGAGA  CAAAGATGAA  GAAGGAGAAT  TTTGAGGGAG  GGGGATTTCT  GAGACATGAT        228

GATAAATATG  TATGTTCTGT  ACATGTCTGA  GATATACAGT  TCTGTTCTCC  AGTAAAGGAC        288

TTGTGAGGTT  CAAAGTGTGA  AGAGATTAAG  GTCTGTTTTT  CTGTGACAAC  TCTGACAGTT        348
```

```
CCAAAGCCAA AAGTCAAATG AAAGAGACTC TCTGTGCTTC CTCTACATGC ATATTTTATG         408

TGGAGCACTT CTAGAGTATG AGTGAAAGAC ATGAACAAAA TAAGTAGAAA AAAATAAGG          468

AAAGAAATTC ACTTCATCGT ATCATTTTTT TACATAACCA ATTAATTCTC TTATTGCA           526

GGA TCC ACT GCA GAT ATT GTG ATG ACG CAG GCT GCA TTC TCC AAT CCA           574
Gly Ser Thr Ala Asp Ile Val Met Thr Gln Ala Ala Phe Ser Asn Pro
            20                  25                  30

GTC ACT CTT GGA ACA TCA GCT TCC ATC TCC TGC AGG TCT AGT AAG AGT           622
Val Thr Leu Gly Thr Ser Ala Ser Ile Ser Cys Arg Ser Ser Lys Ser
        35                  40                  45

CTC CTA CAT AGT AAT GGC ATC ACT TAT TTG TAT TGG TAT CTG CAG AAG           670
Leu Leu His Ser Asn Gly Ile Thr Tyr Leu Tyr Trp Tyr Leu Gln Lys
    50                  55                  60

CCA GGC CAG TCT CCT CAG CTC CTG ATT TAT CAG ATG TCC AAC CTT GCC           718
Pro Gly Gln Ser Pro Gln Leu Leu Ile Tyr Gln Met Ser Asn Leu Ala
65                  70                  75                  80

TCA GGA GTC CCA GAC AGG TTC AGT AGC AGT GGG TCA GGA ACT GAT TTC           766
Ser Gly Val Pro Asp Arg Phe Ser Ser Ser Gly Ser Gly Thr Asp Phe
                85                  90                  95

ACA CTG AGA ATC AGC AGA GTG GAG GCT GAG GAT GTG GGT GTT TAT TAC           814
Thr Leu Arg Ile Ser Arg Val Glu Ala Glu Asp Val Gly Val Tyr Tyr
            100                 105                 110

TGT GCT CAA AAT CTA GAA CTT CCT CGG ACG TTC GGT GGA GGC ACC AAG           862
Cys Ala Gln Asn Leu Glu Leu Pro Arg Thr Phe Gly Gly Gly Thr Lys
        115                 120                 125

CTG GAA ATC AAA CGTAAGTA                                                  882
Leu Glu Ile Lys
    130
```

( 2 ) INFORMATION FOR SEQ ID NO:4:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
            20                  25                  30

Val Thr Leu Gly Thr Ser Ala Ser Ile Ser Cys Arg Ser Ser Lys Ser
        35                  40                  45

Leu Leu His Ser Asn Gly Ile Thr Tyr Leu Tyr Trp Tyr Leu Gln Lys
    50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Arg Thr Phe Gly Gly Gly Thr Lys
        115                 120                 125

Leu Glu Ile Lys
    130
```

( 2 ) INFORMATION FOR SEQ ID NO:5:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

CCCGTTTCAG AATGGAATGT GCAG  24

( 2 ) INFORMATION FOR SEQ ID NO:6:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:6:

CTAAGCTGAA TAGAAGAGAG AGG  23

( 2 ) INFORMATION FOR SEQ ID NO:7:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:7:

TGGGAGAAGT TAGGACT  17

( 2 ) INFORMATION FOR SEQ ID NO:8:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:8:

ATAAAGACCT GGAGAGGCC  19